United States Patent [19]

Ogawa et al.

[11] Patent Number: 4,627,290
[45] Date of Patent: Dec. 9, 1986

[54] METHOD AND APPARATUS FOR DETECTING ACOUSTIC HOMOGENEITY OF OBJECT

[75] Inventors: Toshio Ogawa, Nishitama; Kageyoshi Katakura, Meguro; Shinichiro Umemura, Hachioji, all of Japan

[73] Assignees: Hitachi, Ltd.; Hitachi Medical Corporation, both of Tokyo, Japan

[21] Appl. No.: 723,157

[22] Filed: Apr. 15, 1985

[30] Foreign Application Priority Data

Apr. 13, 1984 [JP] Japan ................................ 59-72838

[51] Int. Cl.$^4$ ............................................. G01N 29/04
[52] U.S. Cl. .................................................... 73/628
[58] Field of Search ......................... 73/628, 598, 627

[56] References Cited

U.S. PATENT DOCUMENTS 3,299,694 1/1967 Dickinson .......................... 73/628

*Primary Examiner*—Anthony V. Ciarlante
*Attorney, Agent, or Firm*—Antonelli, Terry & Wands

[57] ABSTRACT

A pulsating sound wave beam is transmitted into an object using an array-type ultrasonic wave transducer which consists of a plurality of elements; the reflected sound waves are received using said transducer while electronically focusing the reflected sound waves depending upon an estimated speed of sound in the object, and the beam width of sound waves is measured repeatedly near a particular reflector while successively changing the estimated speed of sound. The estimated speed of sound of when the beam width is minimal is the mean speed of sound of the object in practice, and the beam width at that moment serves as an indication of acoustical homogeneity of the object.

4 Claims, 9 Drawing Figures

METHOD AND APPARATUS FOR DETECTING ACOUSTIC HOMOGENEITY OF OBJECT

BACKGROUND OF THE INVENTION

The present invention relates to an ultrasonic diagnostic apparatus of the reflection type, and a method of diagnosis using the apparatus. In particular, the invention relates to a method and apparatus for determining acoustical homogeneity of an object.

The present inventors have developed a method of measuring the speed of sound in an object by utilizing an ultrasonic diagnostic apparatus of the reflection type. A conventional method of measuring the speed of sound by reflection has been disclosed, for example, in D. E. Robinson, et al., "Measurement of Velocity of Propagation from Ultrasonic Pulse-Echo Data", Ultrasound in Med. and Biol., Vol. 8, No. 4, pp. 413–420, 1982. According to this method, ultrasonic wave beams are transmitted from two directions to a reflector in the object as a common target, the time until the waves reflected by the target are received is measured, and a degree of refraction at the interface between the object and an acoustic coupling liquid is estimated from the data thus obtained, thereby to find the speed of sound in the object. This method makes it possible to find the average speed of sound in the object, but is not capable of obtaining data that represent acoustical homogeneity of the object.

SUMMARY OF THE INVENTION

It is a primary object of the present invention to provide a method and apparatus for determining acoustical homogeneity of an object by nondestructive measurement.

In the prior art, a pulsating sound wave is transmitted into the object by an array-type ultrasonic transducer which consists of a plurality of elements, and the reflected sound waves produced by the transmitted sound wave are electronically focused and received such that a focal point of the received wave will conicide with a particular reflector.

The focal distance of the received wave can be so adjusted that the beam width is narrowest at the point of reflection. That is, the focal point of the received wave coincides with the point of reflection on the reflector. It was, however, clarified that concentration of the received wave at the focal point depends upon acoustical homogeneity of the material between the transducer and the focal point. For instance, in an object having regions of high sound velocity and regions of low sound velocity, the beam width near the focal point is wider than that of an acoustically homogeneous object.

Therefore, a first feature of the present invention resides in a method of detecting acoustical homogeneity of an object, comprising:

transmitting a pulsating sound wave into an object using an array-type transducer which consists of a plurality of elements, and receiving the reflected waves produced by said sound wave using said transducer while electronically focusing the reflected waves, the sound waves being transmitted and received repeatedly;

adjusting the degree of said electronic focusing at the time of repeatedly transmitting and receiving the sound wave, such that the focal point of the received wave is made to coincide with the point of reflection on a reflector; and detecting the beam width of the received wave from the reflector that reflects the transmitted wave from the detected signals produced by said transducer after the focal point has been made to coincide with point of reflection on the reflector.

More specifically, the beam width of the received wave at the focal point varies not only with the acoustical homogeneity of the object but also with the distance between the transducer and the reflector on which the point of reflection is located. Therefore, if the beam width obtained by the above-mentioned method is regulated by the distance to the reflector, it is possible to obtain a more generalized indication of acoustic homogeneity of the object.

A second feature of the present invention resides in a method of detecting acoustical homogeneity of an object, comprising:

setting the estimated speed of sound in the object;

transmitting a pulsating sound wave into the object using an array-type transducer which consists of a plurality of elements, and receiving the reflected waves produced by said sound wave using said transducer while electronically focusing the reflected waves in according with said estimated speed of sound;

transmitting and receiving said sound wave repeatedly while changing said estimated speed of sound; and detecting the beam width of the sound wave near the reflector on which the point of reflection is located, each time that said estimated sound speed is changed, and finding the difference between the two estimated sound speeds to obtain a beam width that is greater than the minimum beam width by a predetermined multiple, so as to use the difference between the estimated speeds of sound as an indication of acoustical homogeneity.

Further features of the present invention will become obvious from the following specific description.

DETAILED DESCRIPTION OF THE INVENTION

Figure 1:
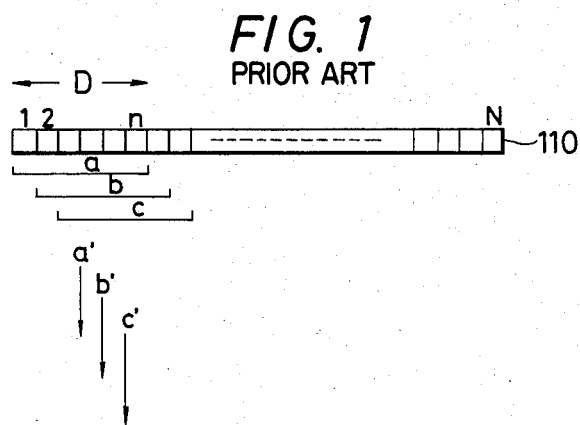
FIG. 1 is a diagram of concept of a conventional reflection-type ultrasonic diagnostic apparatus.

Prior to describing the invention, an outline of a conventional linear-type ultrasonic diagnostic apparatus will be explained blow to facilitate comprehension. As shown in FIG. 1, an array-type transducer 110 consists of a plurality of transducer elements 1 to N. A single transmission and reception of ultrasonic waves is effected by selecting a number of elements (e.g., 1 to n) out of the whole group of elements. Symbol a denotes a transmitting-and-receiving aperture. By shifting the positions of elements for transmitting and receiving the waves as indicated by a, b, c, the center of an ultrasonic wave beam is shifted as indicated by a', b', c'. In the conventional apparatus, apertures of the same size are used for transmitting and receiving the waves; i.e., relatively small apertures are employed from the standpoint of cost and performance.

Figure 2:
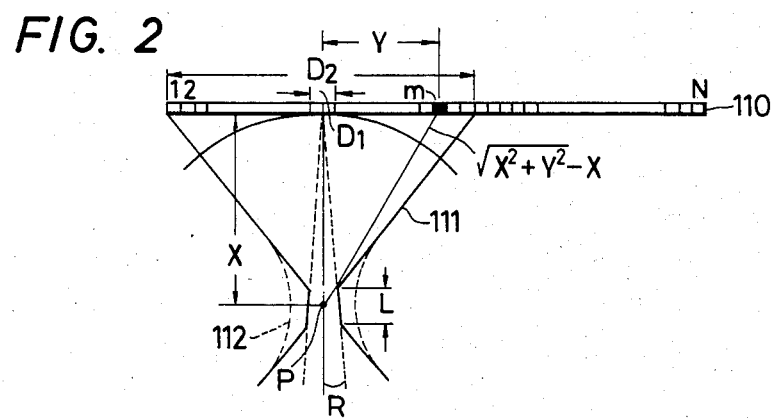
FIG. 2 is a diagram of concept of the principle of the present invention.

FIG. 2 illustrates a principle of the present invention which transmits and receives the waves in the same manner as in FIG. 1, but in which an aperture $D_1$ for transmitting the waves has a diameter different from that of an aperture $D_2$ for receiving the waves, the aperture $D_2$ for receiving the waves being greater than that of the conventional apparatus.

Reception signals obtained from the individual elements in the receiving aperture $D_2$ are suitably delayed and are then added to effect electronic focusing, thereby to obtain a received wave 111 that focuses at a point P at a depth X as shown in FIG. 2. That is, if the sound speed in the object is estimated to be $V_0$, the delay quantity $\tau_0(Y)$ of an element m that is located away from the center of the beam by a distance Y should satisfy the following equation, $$V_0 \tau_0(Y) = \sqrt{X^2 + Y^2} - X \tag{1}$$

The sound wave is more sharply focused by using a transducer having a large aperture than by using a transducer having a small aperture. Therefore, directivity of the transmitted and received waves is for the most part determined by the received wave beam 111, and the resolving power R and depth of focus L are given by the following equations, $$R = \lambda/D_2 \tag{2}$$

$$L = 4\lambda(X/D_2)^2 \tag{3}$$

where $\lambda$ denotes the wavelength of ultrasonic waves that are to be transmitted and received.

For example, when the depth X is 100 mm, the wavelength $\lambda$ is 0.43 mm, and the aperture $D_2$ for receiving the waves has a diameter of 64 mm, the resolving power R is 0.007 (rad) = 0.4 (deg), and the depth of focus L is 4 mm. The beam is transmitted through the small aperture. Therefore, the directivity of the transmitted and received waves is not affected regardless of whether the transmitted wave is electronically focused.

Figure 3:
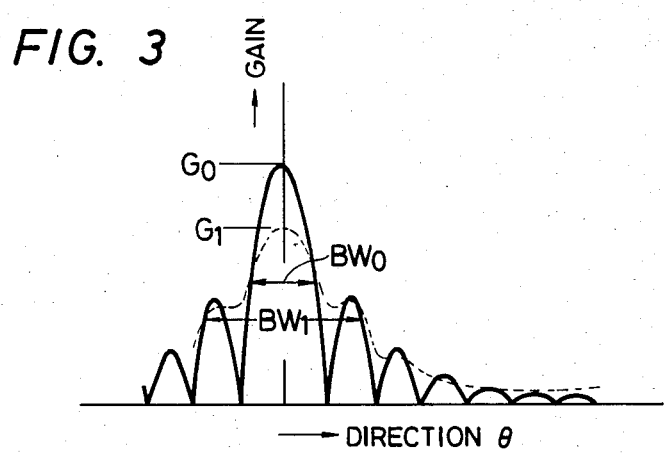
FIG. 3 is a diagram showing directional characteristics of a sound wave.

Thus, the sound wave is very sharply focused near the focal point only when the medium is acoustically homogeneous. When the medium is not homogeneous, the received wave is less sharply focused as designated at 112 in FIG. 2. FIG. 3 shows directivity of the sound wave near the focal point, wherein the abscissa represents the direction $\theta$ and the ordinate represents the gain G. A solid line shows the case when the medium is homogeneous, and a broken line shows the case when the medium is not homogeneous. The maximum gain becomes $G_0$ in the former case, and $G_1$ in the latter case. The ranges in which the gain falls off by, for example, 6 dB relative to the maximum gain is taken as the beam width, and such beam width is denoted by $BW_0$ and $BW_1$ in FIG. 3.

The ultrasonic waves are transmitted and received repeatedly, and the distance X to the focal point is varied after each repetition. That is, the amount of delay $\tau_0(Y)$ of the signal of each element is varied so as to cause the position of focal point to coincide with the reflector in the object. The beam width BW of the received wave is found from the reception signals thus obtained, and is used as an indication of acoustical homogeneity of the object. After the focal point has been made to conicide with the position of the reflector, selection of elements of the transducer 110 is changed, so that center position of the beam transmitted and received is successively shifted in the direction in which the elements are arrayed. Then, a distance at which the gain decreases by 6 dB from the maximum gain of the reception signals is found, to obtain thereby a beam width BW of the received wave.

Figure 4:
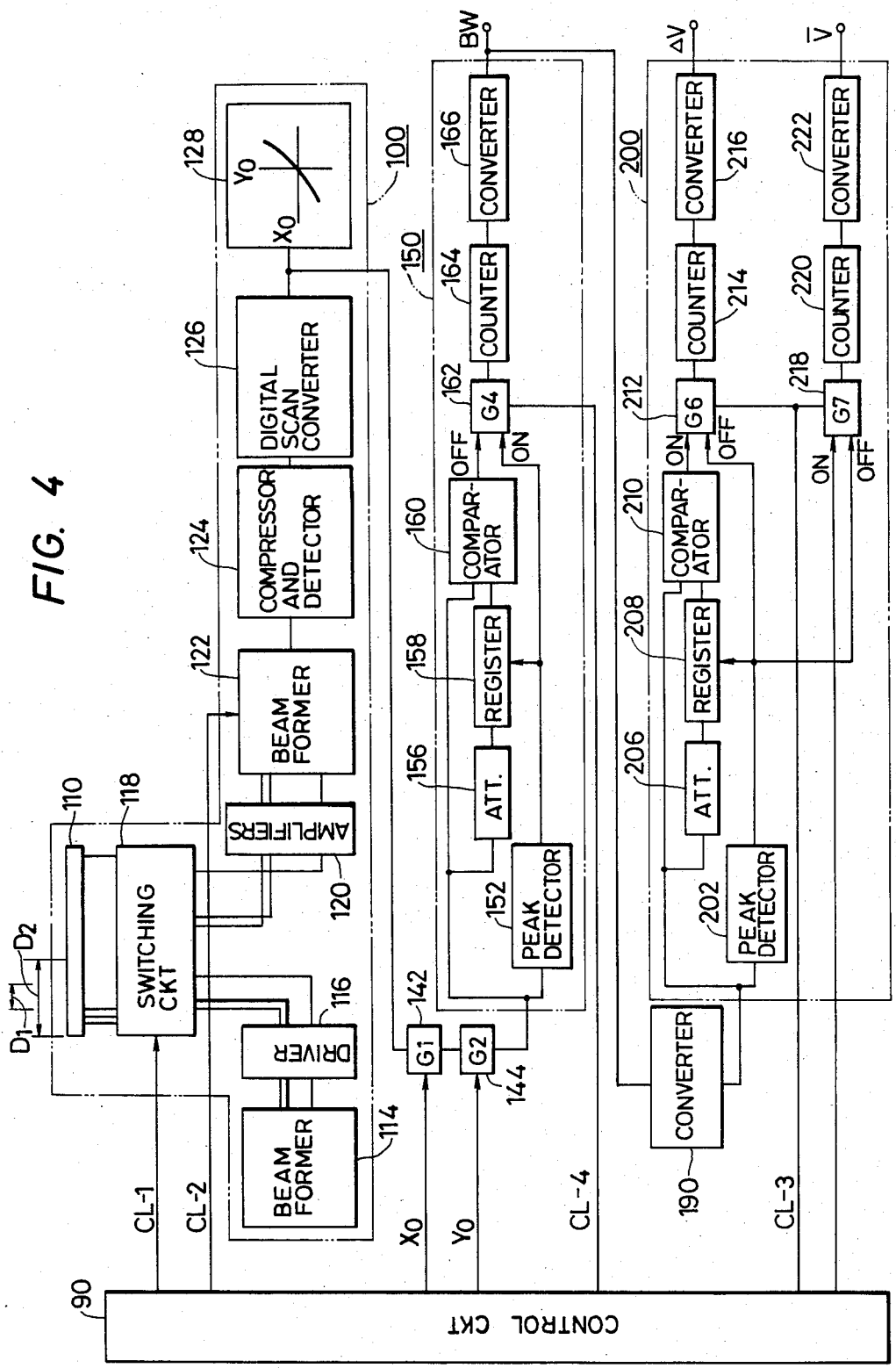
FIG. 4 is a block diagram illustrating an embodiment of the present invention.

FIG. 4 shows a specific apparatus for realizing the method of the present invention.

First, an ultrasonic imaging device 100 will be explained below.

A beam former 114 for transmitting the waves generates a number $n_1$ of RF pulse signals, each having different phases, and sends them to drivers 116. A number $n_1$ of elements that form an aperture $D_1$ for transmitting the waves are selected by a switching circuit 118 among those of a transducer 110, and are driven by the outputs of drivers 116. Reception signals of a number $n_2$ of elements forming an aperture $D_2$ for receiving the waves are supplied, via amplifiers 120, to a beam former 122 that receives the waves. As will be described later, the beam former 122 gives different delays to the reception signals of the elements, and adds the signals to obtain a received beam that is focused at a given point. The added reception signals are compressed and detected by a compressor and detector 124, and are supplied to a digital scan converter 126.

The above-mentioned operation is repeated when a clock signal CL-1 is generated from a control circuit 90. Upon receipt of each clock signal CL-1, the switching circuit 118 changes the selection of elements that participate in transmitting and receiving the waves, such that the center position of the sound wave beam is successively shifted. That is, ultrasonic beam scanning of the type generally known as B-mode scanning is effected, and the data for one picture is stored in the digital scan converter 126 which functions so as to successively read out the reception signals along the Y-axis that are successively written along the X-axis. The stored data is read out in accordance with the order corresponding to picture scanning of a display device 128 of a standard TV system. Thus, an ultrasonogram of the object is displayed on the display device 128.

Figure 5:
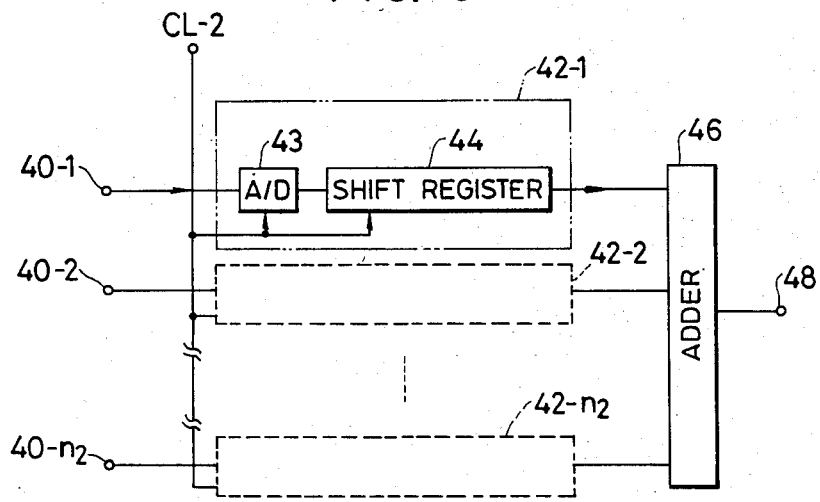
FIG. 5 is a block diagram illustrating a block 122 of FIG. 4.

As shown in FIG. 5, the beam former 122 that receives waves of FIG. 4 consists of delay circuits 42-1, 42-2, ..., 42-$n_2$ of $n_2$ channels, and an adder 46 connected thereto. The delay circuit for each channel consists of an A/D converter 43 and a shift register 44. However, the number of digits in the shift register 44 changes depending upon the channel. The A/D converters and the shift registers are operated by a clock signal CL-2. Therefore, the reception signals of elements supplied through terminals 40-1, ..., 40-$n_2$ are delayed depending upon the frequency of clock pulses CL-2 and the number of digits in the shift registers. The reception signals that are delayed are then totaled in the adder 46 and are produced from a terminal 48.

The control circuit 90 of FIG. 4 contains an operation board (not shown) which specifies a specified point ($X_0$, $Y_0$) on the picture on the display device 128. If the delay quantity $\tau_0(Y)$ of each of the channels satisfies the following equation according to the distance $X_0$ up to the specified point, then the focal point of the received beam is made to coincide with the specific point of aim, $$\tau_0(Y) = \frac{\sqrt{X_0^2 + Y^2} - X_0}{V_0} \quad (4)$$

where,

Y: distance between an element connected to the channel and the center of the beam, $V_0$: speed of sound in the object.

However, the speed of sound $V_0$ (mean speed of sound) in the object is unkown. In the apparatus of this embodiment, therefore, the estimated speed V of sound in the object is successively changed from $V_1$ to $V_n$, and delay quantity of the elements of the delay circuits 42-1, 42-2, ..., 42-$n_2$ is successively changed correspondingly, $$\left.\begin{aligned}\tau_1(Y) &= \frac{\sqrt{X_0^2 + Y^2} - X_0}{V_1} \\ &\vdots \\ \tau_n(Y) &= \frac{\sqrt{X_0^2 + Y^2} - X_0}{V_n}\end{aligned}\right\} \quad (5)$$

Figure 6A:
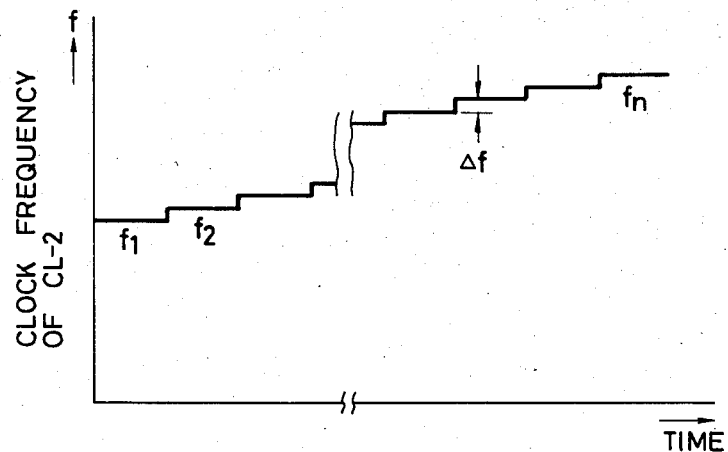
FIGS. 6A and 6B are time charts illustrating the operation of FIG. 4.

To obtain a delay that successively changes as mentioned above, a clock signal CL-2 supplied from the control circuit 90 to the beam former 122 is changed from $f_1$ to $f_n$ maintaining a predetermined period $\Delta f$ of frequency as shown in FIG. 6A. In this case, the following equation holds true between $f_i$ (i=1, 2, ..., n) and $\tau_i(Y)$, $$\tau_i(Y) = k_1 \frac{1}{f_i} \quad (6)$$

where $k_1$ is a constant determined by the design of apparatus.

Figure 6B:
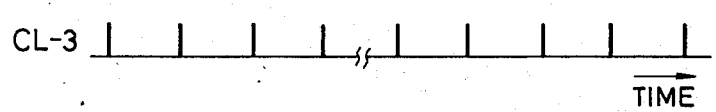

FIG. 6B shows a clock signal CL-3 that is generated each time the frequency of the clock signals CL-2 is changed.

Figure 7:
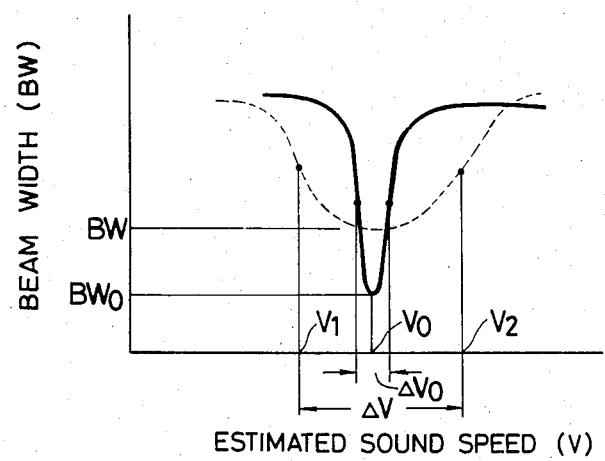
FIGS. 7 and 8 are diagrams of characteristics that illustrate the operation of FIG. 4.

Thus, if the image is taken while successively changing the estimated sound speed in the object, the beam width BW at a depth of the specified point of ($X_0$, $Y_0$) changes as shown in FIG. 7, where a solid line represents the case when the object is homogeneous and a broken line represents the case when the object is not homogeneous. The beam width BW becomes minimum when the estimated sound speed is made to coincide with the mean speed of sound $\overline{V}$ in practice. When the object is homogeneous, furthermore, the beam width changes abruptly. When the object is not homogeneous, however, the beam width changes gradually as shown in FIG. 7. Therefore, a difference $\Delta V$ between the two estimated sound speeds having a beam width twice as great as the minimum beam width, can be used as an index to represent homogeneity. It is considered that the range of difference $\Delta V$ represents a distribution of sound speeds in the object.

A beam width measuring circuit 150 of FIG. 4 automatically measures the beam width BW at a position of the specified point ($X_0$, $Y_0$). Further, a sound speed deviation measuring circuit 200 measures the difference $\Delta V$ and a mean speed of sound $\overline{V}$ in the object relying upon the change in the beam width BW.

Figure 8:
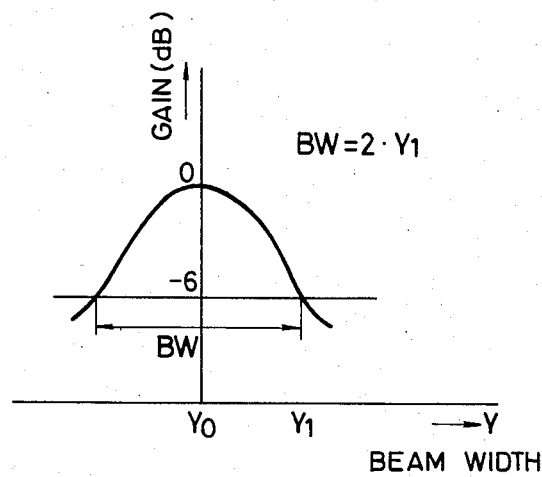

Display signals read from the digital scan converter 126 are input, via gate circuits 142, 144, to the beam width measuring circuit 150. The gate circuit 142 permits only those display signals that correspond to the scanning line of a depth $X_0$ to pass through amoung other display signals. The gate circuit 144, on the other hand, permits only those display signals near a Y-coordinate $Y_0$ of the specified point to pass through among other display signals on the scanning lines. Therefore, the beam width measuring circuit 150 receives only those display signals close to the specified point ($X_0$, $Y_0$) on a scanning line along the Y-axis at a depth on the picture displayed on the display device 128. The display signal has a peak value on the coordinate $Y_0$ as shown in FIG. 8. A peak value detector circuit 152 produces an output when the display signal is at peak value. Responsive to this output, a register 158 stores the value of a display signal input via an attenuator 156 that attenuates the value by 6 dB and, further, a gate circuit 162 is opened. Therefore, a counter 164 starts counting clock signals CL-4 of a predetermined duration. Then, if the intensity of the display signal is smaller than the value stored in the register 158, a comparator 160 produces an output, so that the gate circuit 162 is closed and the counter 164 stops counting. At this moment, the value in the counter 164 represents the elapsed time required for the intensity of display signal on the scanning line to fall off 6 dB from the peak value. A converter 166 multiplies the content of the counter 164 by a predetermined coefficient to convert the time into a pulse width BW.

The above-mentioned operation for measuring pulse width is repeated every time that the frequency of clock signals CL-2 is successively changed from $f_1$ to $f_n$ as shown in FIG. 6A, i.e., repeated each time that the estimated speed of sound in the object is changed starting from $V_1$. The pulse widths $BW_1, \ldots, BW_n$ which are successively obtained are then converted into reciprocal values thereof by a converter 190, and are input to the sound speed deviation measuring circuit 200.

In the sound speed deviation measuring circuit 200, the blocks 202, 206, 208, 210 and 212 are constructed quite in the same manner as the blocks 152, 156, 158, 160 and 162 in the beam width measuring circuit 150. Hence, a counter 214 counts the clock signals CL-3 shown in FIG. 6B. Therefore, when the clock 214 stops counting, the content thereof indicates how many times the clock frequency f has changed from the condition where a reciprocal of the beam width is maximal to a condition where the same reciprocal is halved, i.e., from a condition where the beam width is minimal to a condition where it is doubled.

From the equations (5) and (6), on the other hand, the clock frequency f is proportional to the estimated sound speed V. Therefore, a converter 216 multiplies the value of a counter 214 by a predetermined coefficient to obtain a deviation $\Delta V$ in the estimated speed of sound of FIG. 7.

A counter 220 indicates that many times the clock frequency f is changed starting from $f_1$ before the minimum beam width is obtained. That is, a gate circuit 218 is opened when the measurement is to be started, and permits the clock signals CL-3 to pass through to the counter 220 until the peak detector 202 detects the peak of a reciprocal of a beam width BW. A value of the counter 220 which has ceased to operate responsive to the output of the peak detector 202, is then converted by the converter 222 to obtain an estimated sound speed. The conversion coefficient of the converter 222 is the same as that of the converter 216. The output of the converter 222 represents a true mean sound speed $\overline{V}$ in the object.

In the above-mentioned embodiment, the aperture for receiving the waves is selected so as to be greater than the aperture for transmitting the waves, and the homogeneity of the object is measured relying chiefly upon the directivity of the received wave beam. It is, however, also allowable to employ an aperture of a larger diameter for transmitting the waves and an aperture of a large diameter for receiving the waves to cause the transmitted wave to be focused on a specified point. Namely, it is possible to further sharpen the directivity of both the transmitted waves and the received waves, to increase the precision of measurement.

We claim:

1. A method of detecting the acoustic homogeneity of an object, comprising:

transmitting a pulsating sound wave beam into an object using an array-type transducer which consists of a plurality of elements, and receiving the reflected waves using said transducer while electronically focusing the reflected waves, the sound waves being transmitted and reflected repeatedly;

adjusting the degree of electronic focusing at the time of repetitively transmitting and receiving the sound wave beam so that the focal point of the receive wave beam is made coincident with a specified reflector in said object;

detecting the beam width of the sound wave beam at the specified reflector from the detector signals produced by said transducer after the focal point has been made to coincide with said reflector; and utilizing said detected beam width as an index to represent the acoustical homogeneity of said object.

2. A method of detecting the acoustical homogeneity of an object comprising:

transmitting a pulsating sound wave beam into an object using an array-type transducer formed of a plurality of elements, and receiving the reflected waves using the transducer while electronically focusing the reflected waves to a position of a specified reflector in the object in dependence upon an estimated speed of sound in the object;

repeating the transmission and reception of sound waves while successively changing the estimated speed of sound;

measuring the beam width of the sound wave beam at the specified reflector for each estimated speed of sound;

obtaining a minimum value of the beam width;

obtaining two estimated sound speeds, both of which correspond to beam widths of a predetermined multiple of the minimum beam width; and utilizing a difference between the two estimated sound speeds as an index of the acoustical homogeneity of the object.

3. An apparatus for detecting acoustical homogeneity of an object, comprising:

an array-type transducer formed of a plurality of elements;

wave-transmitting means for producing pulses to drive a set of elements of said ultrasonic transducer so that an ultrasonic wave beam is transmitted into an object;

selecting means for selecting a set of elements of said ultrasonic transducer to be driven for transmitting the ultrasonic wave beam into the object so that reflected signals from the object are received among the plurality of elements of said ultrasonic transducer, said selecting means successively shifting a center position of said set of elements so as to successively shift a center position of the transmitting and receiving ultrasonic wave beams;

focusing means for delaying signals from elements selected by said selecting means in accordance with a focal distance and an estimated speed of sound in the object, and for adding the delayed signals together to provide an added signal indicative of reflected waves detected when a receiving beam is focused at the focal distance;

display means for displaying signals from said focusing means on a plurality of scanning lines, each of said scanning lines corresponding to reflected waves received from different depths of the object;

gate means for selecting a display signal on a scanning line corresponding to the focal distance;

means for successively changing the estimated sound speeds; and means for successively measuring a beam width of the receiving beam by measuring a pulse width of the displayed signals selected by the gate means for every change in the estimated sound speed.

4. An apparatus according to claim 3, further comprising means for calculating the estimated sound speed to obtain a minimum beam width of the ultrasonic waves, and means for calculating a difference between two estimated sound speeds to obtain a beam width of the ultrasonic waves that is a predetermined multiple of the minimum beam width.

* * * * *